United States Patent [19]

Hoxmeier

[11] 4,276,199

[45] Jun. 30, 1981

[54] SUPPORTED MOLYBDENUM/TUNGSTEN COMPOSITIONS

[75] Inventor: Ronald J. Hoxmeier, Houston, Tex.

[73] Assignee: Shell Oil Company, Houston, Tex.

[21] Appl. No.: 170,352

[22] Filed: Jul. 21, 1980

[51] Int. Cl.$^3$ .................... B01J 21/00; B01J 23/24; B01J 27/00
[52] U.S. Cl. .................... 252/438; 252/455 R; 252/447; 252/458; 252/465
[58] Field of Search ............... 252/438, 458, 465, 447

[56] References Cited

U.S. PATENT DOCUMENTS

| | | | |
|---|---|---|---|
| 1,919,730 | 7/1933 | Koenig et al. | 252/458 X |
| 3,167,497 | 1/1965 | Solomon | 252/458 X |
| 3,686,136 | 8/1972 | Doyle | 252/438 X |
| 4,172,053 | 10/1979 | Vogt et al. | 252/447 |

Primary Examiner—Carl F. Dees

[57] ABSTRACT

Novel compositions are prepared by impregnating inert supports with $H_4Mo(CN)_8$ and/or $H_4W(CN)_8$ and subsequently activating by heating in an inert environment at about 400°–600° C. The materials, particularly when supported on aluminous or siliceous supports, are useful as catalysts for simultaneously isomerizing and disproportionating olefins.

8 Claims, 3 Drawing Figures

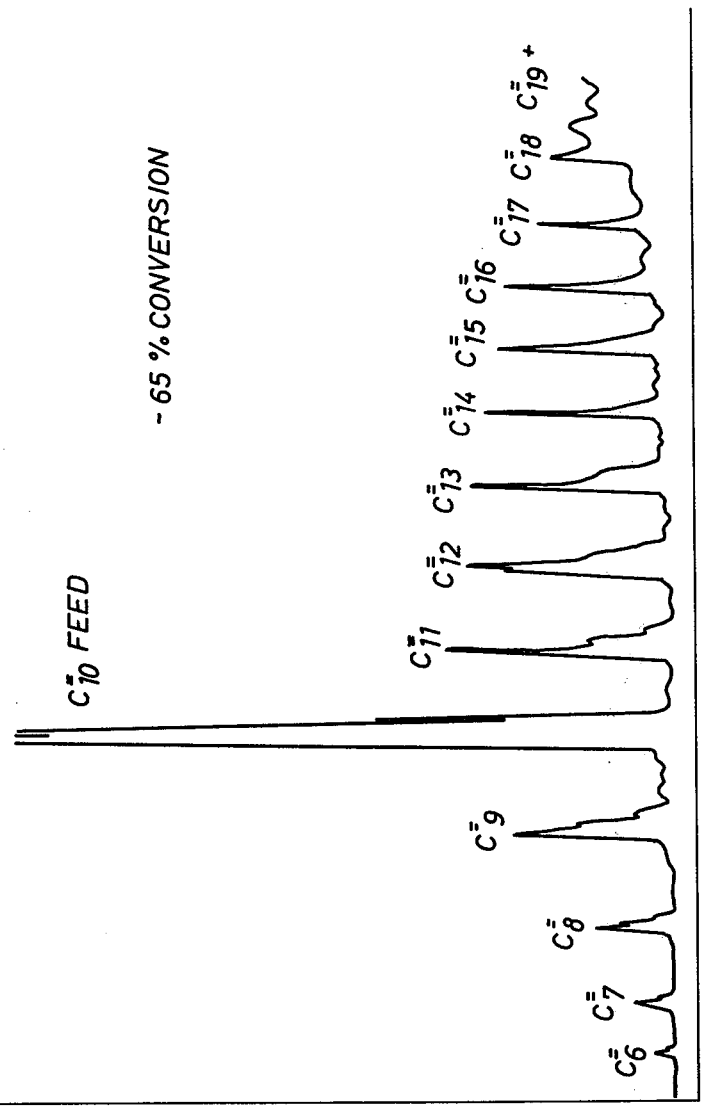

SUPPORTED MOLYBDENUM/TUNGSTEN COMPOSITIONS

FIELD OF THE INVENTION

This invention relates novel supported molybdenum and/or tungsten compositions. These compositions, particularly when utilizing alumina or silica supports are particularly useful for the simultaneous isomerization and disproportionation of olefins.

BACKGROUND OF THE INVENTION

Transition metal carbonyl complexes have long been known for their catalytic activity. The transition metals also form complexes with the cyanide ion which is isoelectronic with the carbonyl. A number of Group VIII metal cyanide complexes are known to catalyze certain organic reactions. For example, $HCo(CN)_5^{-3}$ is capable of selectively hydrogenerating conjugated diolefins to mono-olefins. One attractive property of metal cyanides not possessed by metal carbonyls is their unusually high thermal stability which would allow them to operate in higher temperature regions not practical with metal carbonyls. The compounds $K_4M(CN)_8$ (M=Mo, W) have been known since the 1930's but have not been reported to possess any catalytic properties. Applicant has discovered a method utilizing these alkali metal molybdenum and tungsten cyanides to prepare molybdenum and tungsten compositions having catalytic properties.

SUMMARY OF THE INVENTION

The instant invention relates to novel tungsten/molybdenum compositions and methods for preparation of said compositions. The compositions are prepared by impregnating porous, inert supports with aqueous solutions of $H_4Mo(CN)_8$, $H_4W(CN)_8$ or mixtures thereof, drying the impregnated material, and then calcining the impregnated material in a non-oxidizing environment at a temperature ranging from about 400° to about 600° C. The $H_4Mo(CN)_8$ and $H_4W(CN)_8$ are typically prepared from the alkali metal tungsten/molybdenum octacyanide, for example, $K_4Mo(CN)_8$ and $K_4W(CN)_8$ by ion exchange with the hydrogen form of a strong acid ion exchange resin. The compositions of this invention have unique catalytic properties. Compositions prepared using alumina or silica supports can be used to simultaneously isomerize and disproportionate olefins.

BRIEF DESCRIPTION OF THE DRAWINGS

FIG. 3 illustrates the isomer distribution which results from metathesizing 1-decene using a tungsten/alumina composition.

DESCRIPTION OF THE PREFERRED EMBODIMENTS

Figure 1:
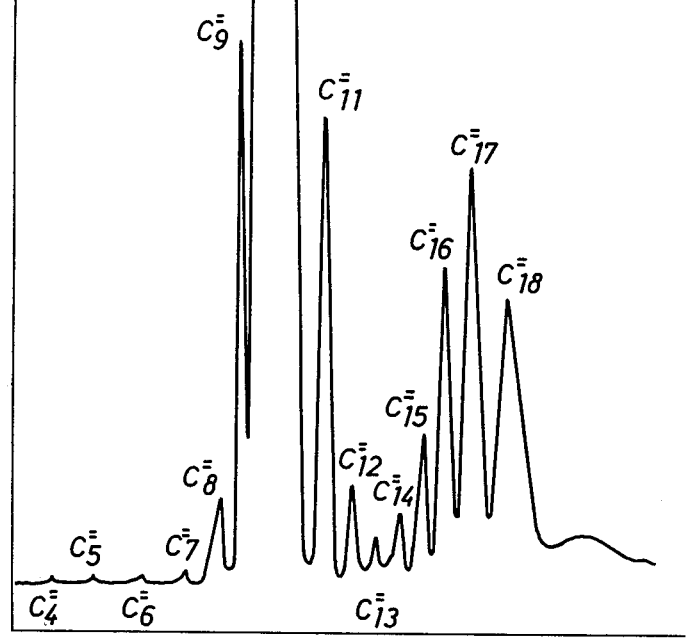
FIG. 1 illustrates the isomer distribution which results from metathesizing 1-decene using a molybdenum/alumina composition.

The compositions of the instant invention are prepared by (1) impregnating a porous inert support with an aqueous solution of $H_4W(CN)_8$, $H_4Mo(CN)_8$ or mixtures thereof; (2) drying the impregnated support and (3) calcining the impregnated support at a temperature ranging from about 400° C. to about 600° C. in a non-oxidizing environment.

The supports utilized to prepare the compositions of this invention must be sufficiently porous to allow impregnation with aqueous solutions of the appropriate cyanide salts. The minium porosity necessary can readily be determined by routine experimentation. The supports must be inert to the preparation techniques used, i.e. they must not decompose, deteriorate or degrade under the impregnation, drying or calcining conditions. If the compositions are being prepared for use in specific catalytic reactions, then the supports should also be inert to the reaction conditions. Examples of suitable supports are carbon, alumina, clay, silica, pumice, magnesia, aluminosilica, zirconia, titania, etc. Preferred supports are aluminas and silicas. The amount of molybdenum and/or tungsten present in the final composition is not critical, but normally will range from about 0.1 to about 25%, preferably from about 1 to about 10 percent by weight of the total composition weight.

The $H_4Mo(CN)_8$ and $H_4W(CN)_8$ used to prepare the impregnating solutions are typically prepared from the corresponding alkali metal octacyanides, e.g. $K_4Mo(CN)_8$ and $K_4W(CN)_8$, by ion exchanging the alkali metal with hydrogen ion using the acid form of strong acid ion exchange resins. Typical useful resins comprise the sulfonated phenolic and styrenic types. The macroreticular sulfonated styrene-divinyl benzene resins are particularly useful.

Impregnation of the supports with aqueous solutions of $H_4Mo(CN)_8$ and $H_4W(CN)_8$ is routine. A preferred technique is the so-called dry-impregnation technique in which only that amount of aqueous solution is used which can readily be absorbed by the support.

After impregnation the support is dried to remove free water. Drying is accomplished in a routine fashion, as for example, passing dry nitrogen or helium or other inert gas over the impregnated support, or by the use of vacuum. The use of an oxidizing environment should be avoided in order to prevent oxidation at the molybdenum or tungsten. The drying step can be combined with the calcining step.

After drying, the impregnated support is calcined in a neutral enviroment at a temperature ranging from about 400° to about 600° C. Times of calcining are not critical typically 0.1–50 hours, lower temperature requiring longer time and vice versa. Suitable examples of a neutral environment are nitrogen, helium argon, vacuum, etc. Nitrogen is preferred.

The compositons of this invention, their preparation and use as catalysts will be further described by the following illustrative embodiments which are provided for illustration and are not to be construed as limiting the invention.

COMPOSITION PREPARATION

Example 1—Molybdenum on alumina $K_4Mo(CN)_8$ was prepared according to the synthesis reported in *Inorganic Synthesis*, Vol. 3, p. 160. 6 Grams of $K_4Mo(CN)_8$ was dissolved in 10 milliters (ml) of $H_2O$ and passed down a strong acid ion exchange column (containing a sulfonated styrene-divinyl benzene resin; amberlite IR-120 HCP, Rohm & Haas Co.), collected in a 50 ml fraction and pulled to dryness under vacuum. The $H_4Mo(CN)_8$ prepared above was dissolved in 10 ml of $H_2O$ and was used as such to impregnate 20 ml of alumina. The resulting material was dried in a vacuum oven overnight at 275° C. Five cc of this material was loaded in a glass reactor tube under $N_2$ and thermally activated under a stream of $N_2$ at 500° C. for 2 hours.

Example 2—Molybdenum on alumina (base treated)

Kaiser A-201 $Al_2O_2$ was refluxed for 1 hour in 5% aqueous KOH solution. The resulting support was then washed liberally with $H_2O$ until the wash solutions were neutral (pH=7). The support was calcined two hours at 500° C. in air.

Then $K_4Mo(CN)_8$ (7 g) was dissolved in 10 ml of $H_2O$ and passed through a strong acid ion exchange column. ($H^+$resin/$K^+$compound=3/1). A 50 ml portion of eluent was collected and reduced to dryness yielding 4.6 g of solid.

2 g of this material was dissolved in 5 ml of $H_2O$ and this solution was used to dry impregnate 10 cc of base-treated Kaiser A-201 $Al_2O_3$. The resulting catalyst was dried in a vacuum oven at 50° C. overnight. This material was placed in a glass reactor tube under $N_2$ (3 cc of catalyst) and heated at 200° C. for 30 minutes, 350° for 30 minutes, then 500° C. for 1 hour.

Example 3—Tungsten in alumina $K_4W(CN)_8$ was prepared according to the synthesis reported in *Inorganic Syntheses* Vol. 7, p. 142 utilizing granular tin. Six grams of $K_4W(CN)_8$ was dissolved in 10 ml of $H_2O$ and passed down a strong acid ion exchange column (Amberlyst IR-120 HCP), collected in a 50 ml fraction and pulled to dryness under vacuum. The $H_4W(CN)_8$ prepared above was dissolved in 10 ml of $H_2O$ and was used to impregnate 20 ml of alumina. The resulting material was vacuum dried overnight at 275° C. and then thermally activated in a stream of $N_2$ at 500° C. for 2 hours.

Example 4—Tungsten/Molybdenum on silica

Similar techniques to those used above were used to prepare compositions comprising molybdenum and tungsten supported on silica (Davison No. 57 $SiO_2$).

Example 5—Tungsten/Molybdenum on carbon

Similar techniques to those used above were used to prepare compositions comprising molybdenum and tungsten in active carbon pellets (Union Carbide—prepared by pyrolysis of polystyrene).

USE OF THE COMPOSITIONS OF THIS INVENTION AS CATALYSTS

The Mo/alumina composition of Example 1 was tested as a catalyst in the metathesis of 1-decene. Five cubic centimeters of the composition was loaded into a glass reactor tube. The tube was heated to 150° C. and 1-decene was fed to the reactor at an LHSV of 3.6 by means of a sage syringe pump (Model No. 255-2) using a 25 ml glass syringe. Product was collected in glass vials immersed in an ice bath. GC analyses showed a 45% conversion of feed with the product containing every olefin from $C_2^=$ through $C_{18}^=$ plus small amounts of some heavier ones. Mass Spec-GC analyses confirmed the products to be the above mentioned olefins and these results are shown in FIG. 1. It is apparent that this composition isomerizes and metathesizes the olefin feed simultaneously.

Figure 2:
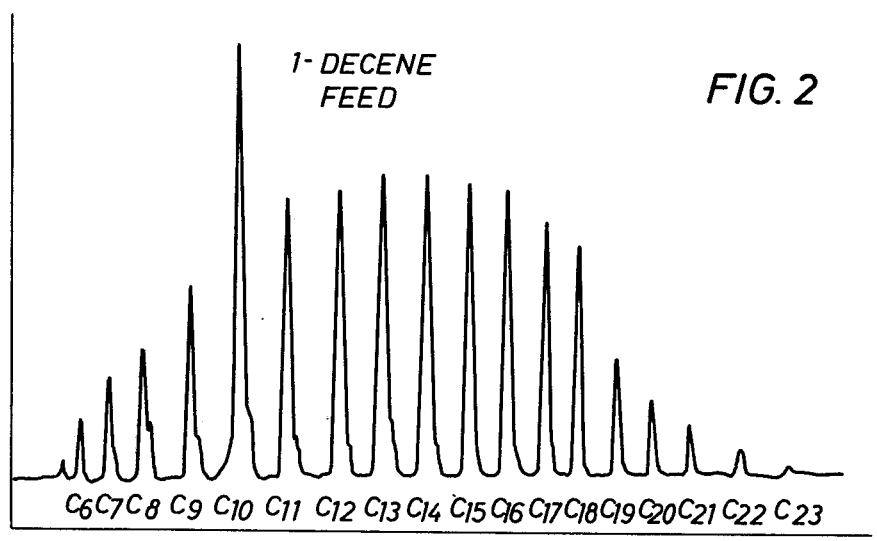
FIG. 2 illustrates the isomer distribution which results from metathesizing 1-decene using a molybdenum/alumina (base-treated) composition.

In order to supress any contribution that the acid character of the alumnia support might contriubute to the isomerization of 1-decene, a molybdenum/alumina composition was prepared using based-neutralized alumina (Example 2 above). This composition was tested for metathesis of 1-decene using the process described above (LHSV=2). GC analyses of the product indicates greater than 90% conversion with extensive isomerization activity. These results are shown in FIG. 2.

Testing the tungsten/aluminia composition of Example 3 under the same conditions that were used for testing the composition of Example 1 gave a conversion of 65% of 1-decene. The results of the GC spectra are shown in FIG. 3.

Testing the tungsten/silica composition of Example 4 under the same conditions that were used for testing the composition of Example 3 gave similar results but lower conversion.

Testing of the molybdenum/carbon showed that this material isomerized 1-decene only and had no metathesis activity.

What is claimed is:

1. A composition prepared by impregnating a porous, inert support with an aqueous solution of $H_4Mo(CN)_8$, $H_4W(CN)_8$ or mixtures thereof, drying the impregnated support and calcining the impregnated support in a non-oxidizing environment at a temperature ranging from about 400° to about 600° C.

2. The composition of claim 1 wherein the support is alumina, silica or mixtures thereof.

3. The composition of claims 1 or 2 where the support is calcined in a nitrogen environment.

4. A process for preparing a molybdenum-and/or tungsten-containing composition which process comprises impregnating a porous, inert support with an aqueous solution of $H_4Mo(CN)_8$, $H_4W(CN)_8$ or mixtures thereof, drying the impregnated support and calcining the impregnated support in a non-oxidizing environment.

5. The process of claim 4 wherein the support is alumina, silica, or mixtures thereof.

6. The process of claim 4 wherein the $H_4Mo(CN)_8$ or $H_4W(CN)_8$ is prepared from the corresponding alkali metal cyanide, $M_4Mo(CN)_8$ (where M=Li, Na, K, Rb or Cs) by ion exchanging said cyanide with the hydrogen form of a strong acid ion exchange resin.

7. The process of claim 6 wherein the ion exchange resin is sulfonated styrene-divinyl benzene resin.

8. The process of claims 4, 5, 6 or 7 wherein the support is calcined in a nitrogen environment.

* * * * *